US012559550B2

(12) United States Patent (10) Patent No.: US 12,559,550 B2

Atwell et al. (45) Date of Patent: Feb. 24, 2026

(54) CRYSTALLIZATION OF ANTIBODIES OR ANTIGEN-BINDING FRAGMENTS

(71) Applicant: Eli Lilly and Company, Indianapolis, IN (US)

(72) Inventors: Shane Krummen Atwell, Carlsbad, CA (US); Ricky Long Lieu, San Diego, CA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 843 days.

(21) Appl. No.: 17/798,629

(22) PCT Filed: Feb. 9, 2021

(86) PCT No.: PCT/US2021/017212
§ 371 (c)(1),
(2) Date: Aug. 10, 2022

(87) PCT Pub. No.: WO2021/163031
PCT Pub. Date: Aug. 19, 2021

(65) Prior Publication Data

US 2023/0137966 A1     May 4, 2023

Related U.S. Application Data

(60) Provisional application No. 62/975,269, filed on Feb. 12, 2020.

(51) Int. Cl.
*C07K 16/00*     (2006.01)
*C07K 16/18*     (2006.01)

(52) U.S. Cl.
CPC ........ *C07K 16/18* (2013.01); *C07K 2317/522* (2013.01); *C07K 2317/55* (2013.01); *C07K 2317/56* (2013.01)

(58) Field of Classification Search
CPC .............. C07K 16/18; C07K 2317/522; C07K 2317/55; C07K 2317/56; C07K 16/00
See application file for complete search history.

(56) References Cited

FOREIGN PATENT DOCUMENTS

| WO | 2014/150973 A1 | 9/2014 |
| WO | 2017/117179 A1 | 7/2017 |
| WO | 2018/118616 A1 | 6/2018 |
| WO | 2019/000105 A1 | 1/2019 |
| WO | WO2023026246 | * | 3/2023 |

OTHER PUBLICATIONS

Slabinski et al, protein Sci, 2007, 16:2472-82 (Year: 2007).*
Chen, Weizao et al., "Improving the CH1-CK heterodimerization and pharmacokinetics of 4Dm2m, a novel potent CD4-antibody fusion protein against HIV-1", MABS, vol. 8, No. 4, Mar. 10, 2016, pp. 761-774.
Lieu, Ricky et al., "Rapid and robust antibody Fab fragment crystallization utilizing edge-to-edge beta-sheet packing", PLOS ONE, vol. 15, No. 9, Sep. 11, 2020.
Raheleh Toughiri et al., "Comparing domain interactions within antibody Fabs with kappa and lambda light chains", MABS, vol. 8, No. 7, Jul. 25, 2016, pp. 1276-1285.
International Search Report, PCT/US2021/017212, mailed on May 31, 2021 by the European Patent Office; 7 pages.
Written Opinion of the International Searching Authority, PCT/US2012/017212, mailed on May 31, 2021 by the European Patent Office; 8 pages.

* cited by examiner

*Primary Examiner* — Lei Yao
(74) *Attorney, Agent, or Firm* — Xiaoguang Gao

(57) ABSTRACT

Provided herein are methods and compositions for improving the crystallization of antibodies, antigen-binding fragments, e.g., Fab or Fab', or fusion proteins, and Fab/Fab'/mAb: Antigen complexes.

13 Claims, 9 Drawing Sheets

Specification includes a Sequence Listing.

Human Kappa　$_{197}$THQGLSSPV$_{205}$ (SEQ ID NO: 1 <u>residues 90-98</u>)

Mouse Kappa　　THKTSTSPI (SEQ ID NO: 13 <u>residues 90-98</u>)

Rabbit Kappa　T-QGTTS-V (SEQ ID NO: 14 <u>residues 89-95</u>)

Human Lambda　T-HEGST-V (SEQ ID NO: 15 <u>residues 90-96</u>)

Mouse Lambda　T-HEGHT-V (SEQ ID NO: 16 <u>residues 89-95</u>)

Rabbit Lambda T-HEGHT-V (SEQ ID NO: 17 <u>residues 89-95</u>)

200mM Ammonium tartrate dibasic + 40% PEG 3350

40% PEG 3350 + 200mM Potassium Sodium Tartrate

40% PEG 3350 + 200mM Potassium Chloride

40% PEG 3350 + 200mM Potassium Phosphate

CRYSTALLIZATION OF ANTIBODIES OR ANTIGEN-BINDING FRAGMENTS

The present application is being filed along with a Sequence Listing in ST25 format. The Sequence Listing is provided as a file titled "X22176_US_ST25.txt" created Sep. 29, 2025, and is 18 kilobytes in size. The Sequence Listing information in the ST25 format is incorporated herein by reference in its entirety.

FIELD OF THE INVENTION

The present disclosure relates to methods and compositions for improving the crystallization of monoclonal antibodies (mAbs) or antigen-binding fragments, e.g., Fab or Fab', or fusion proteins, and Fab/Fab'/mAb: Antigen complexes.

BACKGROUND

Antibody therapeutics are one of the most important classes of drugs. By the end of 2019, 90 monoclonal antibody drugs treating immune disease, infection disease, cardiovascular disease, cancer and others had been approved in the United States and Europe, accounting for $115B sales in 2018 (Kaplon, et al., Mabs, 2020. 12 (1): 1703531; Lu, et al. J Biomed Sci. 2020; 27:1). While at one time, rodent antibodies were developed for human use, this was followed by a long period of humanized antibodies, which over the last two decades has shifted to entirely human discovery platforms like phage and yeast display (Parmley and Smith, Gene, 1988. 73 (2): 305-18; Boder and Wittrup, Nat. Biotechnol., 1997. 15 (6): 553-7) or by immunization of rodents with human germline repertoires (Lonberg, Handb. Exp. Pharmacol., 2008. (181): 69-97). In these platforms, engineering is not necessary for humanization but continues to be used to address other issues: affinity, cross-reactivity, post translational modifications, hydrophobicity, electrostatics, viscosity, and immunogenicity. Furthermore, characterization of antibodies continues to become more sophisticated, especially as new antibody derived formats are developed like antibody drug conjugates and bispecific antibodies (Carter and Lazar, Nat. Rev. Drug Disc., 2018. 17 (3) 197-223).

Modeling of antibody structures has become an integral part of predicting the behavior of potential therapeutics, especially for properties such as hydrophobicity, stability, charge/dipole moments and deamidation propensity (Xu Y, et al., Mabs, 2019. 11 (2) 239-264). This modeling is typically based on publicly available crystal structures. Due to the difficulty of modeling CDR structures, especially heavy chain CDR3, modeling on the crystal structures of highly similar (or identical) Fab crystal structures should improve the accuracy of predictions of antibody properties. Where available high-resolution Fab structures would provide the best basis for calculations.

Structures of Fab: Antigen complexes have even greater value. They can supply the crystal structure of the Fab for the above and also epitope: paratope information. Obtaining the Fab: Antigen complex structures is the only way to directly determine the relative 3-dimensional positions of the antigen and Fab to the precision of individual atoms. Epitopes can be seen, rather than inferred. Amino acid side chains can be examined, and hypotheses formed regarding their roles in affinity and cross-reactivity and calculations conducted to predict and engineer affinity (up or down) and cross-reactivity. In addition, the structure of Fab: Antigen complex can be referenced when considering other mutations and can be an essential cross-check in determining the validity of different assay formats.

However, crystal structure determination is challenging and costly (Slabinski, et al., Protein Sci, 2007. 16 (11): 2472-82). The most difficult step tends to be the production of well-ordered crystals from purified protein. There are many factors that may hinder the crystallizability of a protein: purity, stability, disorder (inter domain, loop or termini), surface charge and hydrophobicity, etc. (McPherson, Crystallization of biological macromolecules, 1999. Cold Spring Harbor Laboratory Press, Cold Spring Harbor, NY). Obtaining well diffracting crystals can take a few days or a few years or might simply be abandoned after significant effort.

While the crystallization and structure determination of Fabs is easy relative to many other protein classes, especially membrane proteins, broad screening and optimization of crystallization methodology is still necessary. Like other proteins, some Fabs require significant crystal optimization and examples of entirely recalcitrant Fabs exist. Fab: Antigen complexes are often easier to crystallize than the antigen alone (hence the use of Fabs as "crystallization chaperones") (Griffin, et al., Clin. Exp. Immunol., 2011. 165 (3): 285-91) but can still be difficult and require extensive screening and optimization. The individual attention across days to months required in crystallization and structure refinement make these two steps the most expensive in the process from sequence to final structure. Difficult cases are especially and negatively impactful to overall averages. The effort required for Fab crystallization perhaps explains why so few structures have been used for engineering or calculations.

Edmundson and Borrebaeck examined the crystal packing interaction and the β-sheet formation between the light chain constant domain (CL) and the heavy chain first constant domain (CH1) of human Fabs, and observed the importance of the "packing triads," three alternating residues with a propensity to form beta sheets. (Edmundson and Borrebaeck, Immunotechnology, 1998. 3 (4): 309-17).

There exists a need for improving the crystallization of Fabs, e.g., human Fabs, comprising a human CL domain of κ chain and/or human Fab: Antigen complexes.

DETAILED DESCRIPTION

Provided herein are methods and compositions that significantly improve the crystallization of human antibodies, antigen-binding fragments (e.g., human Fab or Fab') or fusion proteins comprising a human antibody light chain kappa constant domain (Cκ), and the Fab/Fab'/mAb: Antigen complexes. The methods and compositions described herein can be universally applied to most human Fabs, some human mAbs, and fusion proteins comprising a human Fab or mAb, which comprise human Cκ, and significantly improved their crystallization, including rendering them more likely to crystallize quicker, to a higher resolution, at a lower concentration and/or from a heterogeneous mixture.

In one aspect, provided herein are antibodies, antigen-binding fragments (e.g., human Fab or Fab') or fusion proteins comprising a variant Cκ, wherein the variant Cκ comprises amino acids QGTTS (SEQ ID NO: 20) at positions 199 to 203 of human Cκ (positions numbered according to Kabat numbering, which correspond to positions 92 to 96 of SEQ ID NO: 1), and the amino acids at positions 198 and 204 of human Cκ (positions numbered according to Kabat numbering, which correspond to positions 91 and 97 of SEQ ID NO: 1) are deleted in the variant Cκ. In some embodiments, the variant Cκ further comprises an alanine at position 126 (according to Kabat numbering, which correspond to position 19 of SEQ ID NO: 1) of human Cκ. In some embodiments, the variant Cκ further comprises proline at position 214 (according to Kabat numbering, which correspond to position 107 of SEQ ID NO: 1) of human Cκ.

Unless otherwise specified, the numbering of the amino acid residues in the antibodies or antigen-binding fragments described herein follows the Kabat numbering system (Kabat et al, Sequences of Proteins of Immunological Interest, 5th edition, Bethesda, MD: U.S. Dept. of Health and Human Services, Public Health Service, National Institutes of Health, 1991).

In some embodiments, provided herein are antibodies, antigen-binding fragments (e.g., human Fab or Fab') or fusion proteins comprising a variant Cκ domain that comprises SEQ ID NO: 3. In some embodiments, provided herein are antibodies, antigen-binding fragments (e.g., human Fab or Fab') or fusion proteins comprising a variant Cκ domain that comprises SEQ ID NO: 4. In some embodiments, provided herein are antibodies, antigen-binding fragments (e.g., human Fab or Fab') or fusion proteins comprising a variant Cκ domain that comprises SEQ ID NO: 5. In some embodiments, provided herein are antibodies, antigen-binding fragments (e.g., human Fab or Fab') or fusion proteins comprising a variant Cκ domain that comprises SEQ ID NO: 6.

In some embodiments, the antibodies, antigen-binding fragments (e.g., human Fab or Fab') or fusion proteins further comprise a human light chain variable domain (VL) and a human heavy chain variable domain (VH). In some embodiments, the antibodies, antigen-binding fragments (e.g., human Fab or Fab') or fusion proteins further comprise a human IgG CH1 domain, e.g., a human IgG1 or IgG4 CH1 domain. In some embodiments, the antibodies, antigen-binding fragments (e.g., human Fab or Fab') or fusion proteins further comprise a portion of human IgG hinge region, e.g., a human IgG1 or IgG4 hinge region.

In another aspect, provided herein is a library of antibodies, antigen-binding fragments (e.g., human Fab or Fab') or fusion proteins comprising a variant Cκ, wherein the variant Cκ comprises amino acids QGTTS (SEQ ID NO: 20) at positions 199 to 203 of human Cκ, and the amino acids at positions 198 and 204 of human Cκ are deleted in the variant Cκ (all positions numbered according to Kabat numbering).

In another aspect, provided herein are methods of generating a crystal structure of an antibody, antigen-binding fragment (e.g., human Fab or Fab') or fusion protein comprising a variant Cκ described herein. Such methods can comprise crystallizing the antibody, antigen-binding fragment or fusion protein comprising the variant Cκ, wherein the variant Cκ comprises amino acids QGTTS (SEQ ID NO: 20) at positions 199 to 203 of human Cκ, and the amino acids at positions 198 and 204 of human Cκ are deleted in the variant Cκ (all positions numbered according to Kabat numbering). In some embodiments, the methods further comprise constructing a library of antibodies, antigen-binding fragments (e.g., human Fab or Fab') or fusion proteins comprising a variant Cκ described herein. For example, the variant Cκ can comprise amino acids QGTTS (SEQ ID NO: 20) at positions 199 to 203 of human Cκ, and the amino acids at positions 198 and 204 of human Cκ are deleted in the variant Cκ (all positions numbered according to Kabat numbering). In some embodiments, the variant Cκ comprises SEQ ID NO: 3. In some embodiments, the variant Cκ comprises SEQ ID NO: 4. In some embodiments, the variant Cκ comprises SEQ ID NO: 5. In some embodiments, the variant Cκ comprises SEQ ID NO: 6.

Also provided herein are methods of generating a crystal structure of an antibody, antigen-binding fragment (e.g., human Fab or Fab') or fusion protein comprising human Cκ domain. Such methods can include: generating an antibody, antigen-binding fragment (e.g., human Fab or Fab') or fusion protein comprising a variant Cκ, wherein the variant Cκ comprises amino acids QGTTS (SEQ ID NO: 20) at positions 199 to 203 of human Cκ, and the amino acids at positions 198 and 204 of human Cκ are deleted in the variant Cκ (all positions numbered according to Kabat numbering); and crystallizing the antibody, antigen-binding fragment (e.g., human Fab or Fab') or fusion protein comprising the variant Cκ. In some embodiments, the variant Cκ further comprises an alanine at position 126 (according to Kabat numbering) of human Cκ. In some embodiments, the variant Cκ further comprises proline at position 214 (according to Kabat numbering) of human Cκ. In some embodiments, the variant Cκ comprises SEQ ID NO: 3. In some embodiments, the variant Cκ comprises SEQ ID NO: 4. In some embodiments, the variant Cκ comprises SEQ ID NO: 5. In some embodiments, the variant Cκ comprises SEQ ID NO: 6.

In another aspect, provided herein are methods of generating a crystal structure of a complex of an antigen and an antibody, antigen-binding fragment or fusion protein that binds the antigen (e.g., human Fab or Fab'), wherein the antibody, antigen-binding fragment (e.g., human Fab or Fab') or fusion protein comprises human Cκ, the method comprising: generating an antibody, antigen-binding fragment (e.g., human Fab or Fab') or fusion protein comprising a variant Cκ, wherein the variant Cκ comprises amino acids QGTTS (SEQ ID NO: 20) at positions 199 to 203 of human Cκ, and the amino acids at positions 198 and 204 of human Cκ are deleted in the variant Cκ (all positions numbered according to Kabat numbering); and co-crystallizing the antigen and the antibody, antigen-binding fragment (e.g., human Fab or Fab') or fusion protein comprising the variant Cκ. In some embodiments, the variant Cκ further comprises an alanine at position 126 (according to Kabat numbering) of human Cκ. In some embodiments, the variant Cκ further comprises proline at position 214 (according to Kabat numbering) of human Cκ. In some embodiments, the variant Cκ comprises SEQ ID NO: 3. In some embodiments, the variant Cκ comprises SEQ ID NO: 4. In some embodiments, the variant Cκ comprises SEQ ID NO: 5. In some embodiments, the variant Cκ comprises SEQ ID NO: 6.

As used herein, the term "a," "an," "the" and similar terms used in the context of the present disclosure (especially in the context of the claims) are to be construed to cover both the singular and plural unless otherwise indicated herein or clearly contradicted by the context.

The term "antibody," as used herein, refers to an immunoglobulin molecule that binds an antigen. Embodiments of an antibody include a monoclonal antibody, polyclonal antibody, human antibody, humanized antibody, or chimeric antibody. The antibodies can be of any class (e.g., IgG, IgE, IgM, IgD, IgA) and any subclass (e.g., IgG1, IgG2, IgG3, IgG4).

An exemplary antibody is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212).

The term "antigen-binding fragment" refers to a portion of an antibody that retains the ability to specifically interact with an epitope of an antigen. Examples of antigen binding fragments include, but are not limited to, Fab or Fab'. A "Fab" fragment consists of an entire antibody light chain comprising the light chain variable region (VL) and the light chain constant region (CL), along with the heavy chain variable region (VH) and the heavy chain first constant domain (CH1). Each Fab fragment is monovalent with respect to antigen binding, i.e., it has a single antigen-binding site. A Fab' fragment differs from the Fab fragment by having a few additional residues at the carboxyl terminus of the CH1 domain including one or more residues from the antibody hinge region. A Fab or Fab' described herein can be a human Fab or Fab' or a chimeric Fab or Fab' that comprises a human CL.

The term "fusion protein," as used herein, refers to a recombinant protein comprising a human antibody or antibody fragment connected directly to a heterologous peptide or polypeptide at the amino or carboxyl terminus of either the heavy chain or the light chain of the human antibody or antibody fragment.

BRIEF DESCRIPTION OF THE DRAWINGS

FIG. 1A shows the HC:HC and LC:LC beta packing in 4ZTO.pdb. Heavy chain in black and light gray. Light chain in dark gray and white. FIG. 1B shows HC:LC beta packing in 4JO1.pdb.

FIG. 2A shows the structural alignment of the human Fab from 4NZU.pdb (dark gray) on the rabbit Fab crystal packing from 4ZTO (medium and light gray), which shows that the rabbit Cκ FG loop (medium gray) is more compact and compatible with the beta sheet packing than the longer and bulging human Cκ FG loop would not be. FIG. 2B shows sequence alignment of FG loops of human, mouse and rabbit Cκ domains and Cλ domains. Rabbit FG loop is two residues shorter, which resembles the FG loop from the Cλ domains. FIG. 2C shows the second potential site of interference is the human K126 sidechain.

FIG. 3A shows the crystal packing in the dupilumab parental Fab. No G strand beta packing is present. FIG. 3B shows one plane of crystal packing in crystal kappa version. Each kappa constant (light gray) forms a beta sheet with a nearby CH1 domain (black). FIG. 3C shows the beta sheet formed between the G strand of the Cκ domain (white) and the G strand of the CH1 domain (dark gray). Sheet extends from Cκ T205 to S211 and CH1 N216 to R222 (residues numbered sequentially in the crystal structure), which is pseudo-symmetric and centered between the Cκ V208 (position 205 according to Kabat numbering) and CH1 V219 (Kabat numbering).

FIG. 4A shows the crystal structures of the Crystal Kappa version of dupilumab Fab (top right) complexed with human IL4R extracellular domain. FIG. 4B shows the crystal structures of the Crystal Kappa version of human IL17 dimer (top middle) complexed with secukinumab Fabs.

FIG. 5A shows the chromatogram. FIG. 5B shows the images of every crystallization drop at day 9. FIG. 5C shows the score assigned to each condition, where anything crystalline is scored at 90 or higher.

FIG. 6A is an image showing the crystals of the full-length mAb. FIG. 6B is a ribbon diagram of the resulting structure with the antibody heavy chain in black (including Fc glycosylation in sticks) and antibody light chain in light gray.

FIG. 7A is an image showing the crystals of the Crystal Kappa light chain of L14H18 fused to the Tau peptide after four hours. FIG. 7B is a ribbon diagram of the resulting 2.3 Å structure of the Tau peptide (white) bound to L14H18 Fab with a mostly ordered Gly-Ser linker to the N-terminus of the Fab light chain (gray). Fab heavy chain is shown in black.

EXAMPLES

Example 1: Crystallization of Fabs and Fab: Antigen Complexes

Analysis of Rabbit Fab Crystal Packing and Design of Human Crystallizable Kappa

Figure 1A:
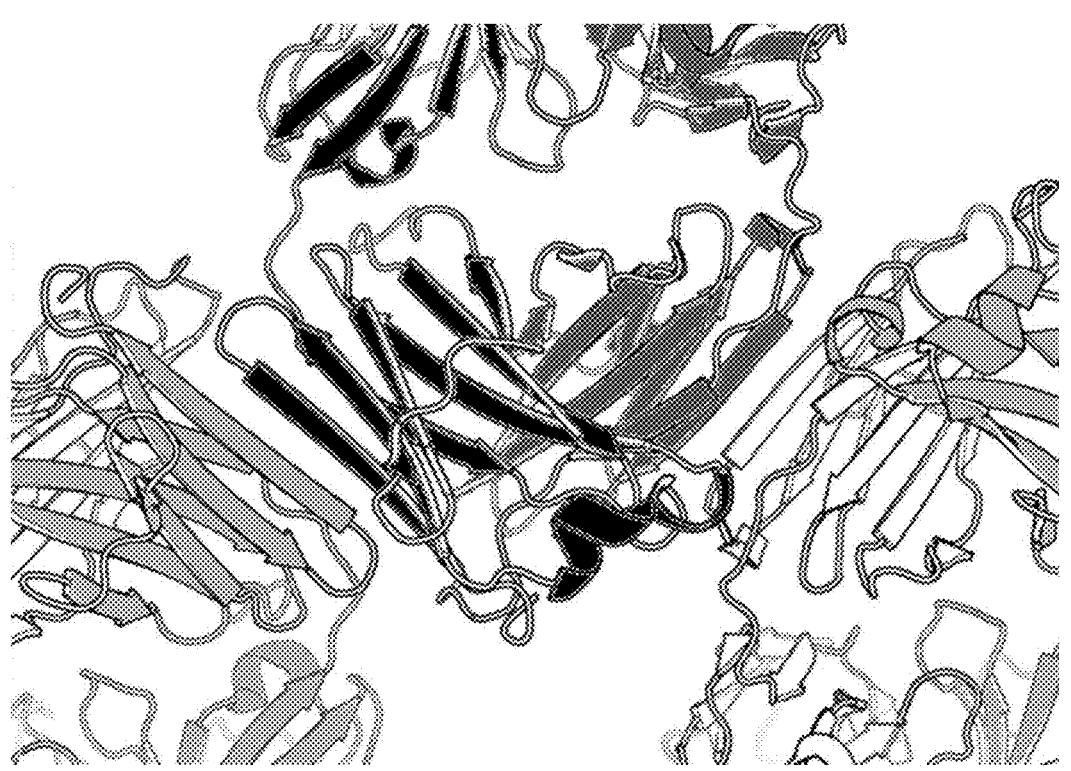
FIGS. 1A-1B show exemplary G-strand beta sheet packing in rabbit Fab crystal structures.

Visual inspection of the crystal packing interactions in 36 published and proprietary rabbit Fab crystal structures show that constant domain beta-strand to beta-strand crystal packing is common (Table I). In 68% of the 19 deposited rabbit Fab structures (including Fab complexes) a LC to LC beta interaction occurs, forming a continuous beta sheet across two Fab molecules (FIG. 1A). Over a third of those structures also have a HC:HC beta packing interaction. Overall, 84% of the structures form some kind of beta sheet packing interaction in the G strand of the constant domains. The in-house experience is similar but with more examples of Fabs that have both HC:HC and LC:LC crystal packing interactions and fewer examples that have HC:LC packing (Table I and FIG. 1B). Crystals of Fabs that form both the HC:HC and LC:LC or that form HC:LC packing interactions have a continuous column of constant domains, each domain forming a typical Fab HC:LC interaction as well as a beta sheet with another domain.

TABLE 1

F-strand beta sheet crystal packing of rabbit
Fab and Fab complex structures.

| PDB* | Resolution | HC:HC | LC:LC | HC:LC |
|---|---|---|---|---|
| 4HBC | 1.54 | | X | |
| 4JO1 | 2.03 | | | X |
| 4JO2 | 2.50 | | | X |
| 4JO3 | 2.60 | X | X | |
| 4JO4 | 2.27 | X | X | |
| 4ZTO | 2.30 | X | X | |
| 4ZTP | 1.63 | | X | |
| 5DRN | 1.99 | | X | |
| 5DS8 | 1.95 | | X | |
| 5DSC | 2.40 | | X | |
| 5DTF | 1.90 | X | | |
| 5DUB | 2.00 | | | |
| 5M63 | 2.74 | X | X | |
| 5V6L | 2.55 | X | X | |
| 6CEZ | 2.40 | | | |
| 6CJK | 1.80 | | X | |
| 6I9I | 1.98 | | | X |
| 6PEH | 2.30 | X | X | |
| 6T3F | 3.20 | | X | |
| PDB Total | 19 | 37% | 68% | 16% |
| HC:HC & LC:LC | 6 | 32% | | |
| Any | 17 | 84% | | |
| Lilly Internal | 17 | 29% | 59% | 6% |
| HC:HC & LC:LC | 10 | 59% | | |
| Any | 14 | 82% | | |

*Percentage of deposited PDB structures with either HC:HC, LC:LC or HC:LC G-strand beta sheet formation. Also indicated are percentage with both HC:HC and LC:LC packing as well as percentage of structures with any G-strand beta packing. Lilly internal statistics are listed below PDB statistics.

Figures 2A, 2B:
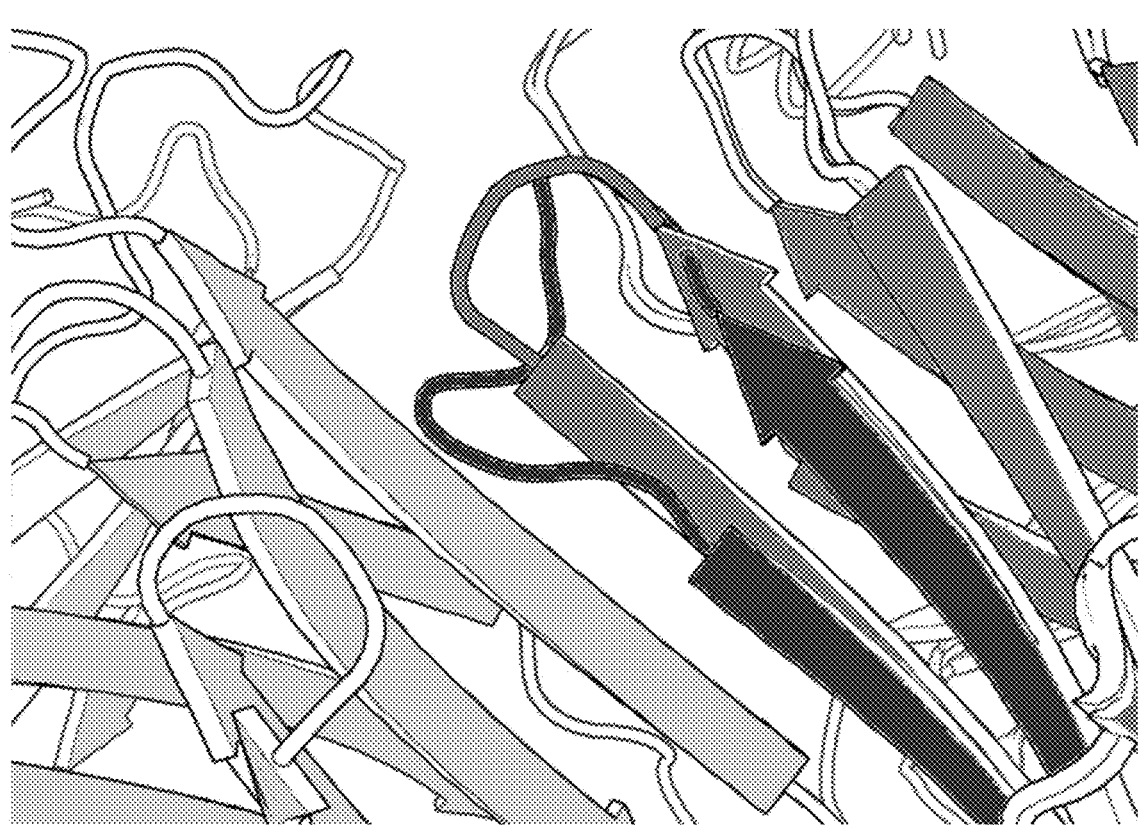
FIGS. 2A-2C show the incompatibility of human Cκ FG loop with rabbit like LC:LC packing.
Figure 2C:
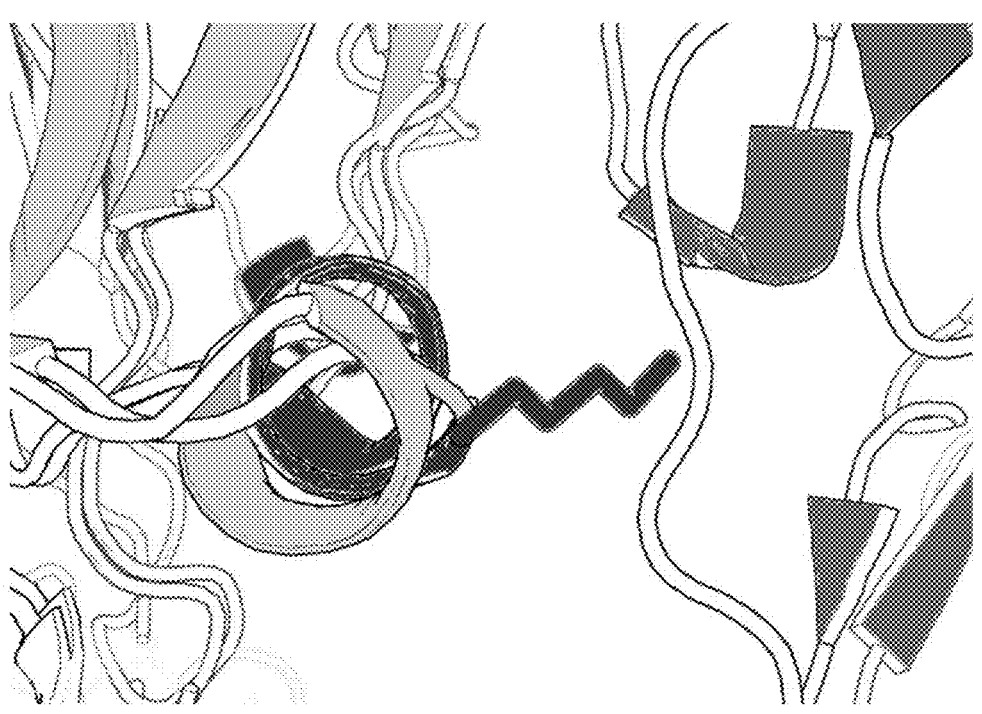

A survey of dozens of human Fab structures shows no such interactions. Alignment of a human Fab structure onto a rabbit Fab shows that the longer FG loop present in human Cκ domains forms a bent and bulging conformation that would interfere with a beta sheet packing interaction (FIG. 2A). This longer FG loop is shared by mouse Cκ but not by rabbit Cκ domain (nor by the lambda constant domains Cλ) (FIG. 2B). Visual inspection of the human Fab aligned on the rabbit packing interaction also suggests that the human Cκ lysine 126 (K126, Kabat numbering) might be an impediment to beta sheet packing on the opposite side of the domain (FIG. 2C).

Several variants of a hexahistidine (H6) tagged Fab fragment are generated by mutating the FG loop or K126 of Cκ and tested their impacts on crystallization. In the case of the FG loop, this consists of replacing the septamer human sequence HQGLSSP (SEQ ID NO: 23) (positions 198 to 204 according to Kabat numbering) between the structurally homologous T and V (position 197 and 205, respectively, according to Kabat numbering), with the pentamer rabbit sequence QGTTS (SEQ ID NO: 20) (positions 199 to 203 according to Kabat numbering). The resulting mutant is shorter by two residues, with deletions of histidine at position 198 and proline at position 205, and is referred to herein as ΔQGTTSΔ (SEQ ID NO: 20) (positions 198 to 204 according to Kabat numbering, see SEQ ID NO: 3) or the "Crystal Kappa" design. In some variants, K126 is mutated to alanine (K126A, Kabat numbering, see SEQ ID NOs: 2, 4, 6). Separately to the crystal packing analysis, it is observed that the C-terminal interchain disulfide is rarely ordered in Fab structures. This could be due to conformational heterogeneity or due to heterogeneous oxidation. To address this, two variants are designed. One variant called "GEP*" is generated by removing the disulfide bond by mutating the C-terminal kappa chain cysteine to proline (C214P according to Kabat numbering, see SEQ ID NO: 5 or 6) and the IgG4 heavy chain cysteine 127 to alanine (C127A according to Kabat numbering). The second design called "ESKCGGH6" (SEQ ID NO: 22) is generated by mutating the kappa cysteine to proline (C214P according to Kabat numbering) and creating a new disulfide partner at the C-terminus of the heavy chain by mutating Tyr 229 to Cysteine (Y229C according to Kabat numbering).

Crystallization of Fabs

The crystallization results of two Fabs (G6 and dupilumab) before and after incorporating these mutations either alone or in combination are shown in Table II. One Fab is derived from the published Dupilumab (Dupixent™) sequence (available at https://www.kegg.jp/entry/D10354). The second Fab is part of an internal discovery effort against a cell surface receptor. Two 96-well crystallization screens are used with Fabs purified identically, set up at approximately 10 mg/ml, streak seeded with unrelated Fab crystals (in order to eliminate stochastic differences due to nucleation) and analyzed at the same time point (9 days). Both parental Fabs produce crystalline hits in a few conditions and the dupilumab Fab crystals even yield a 2.0 Å dataset and structure. Neither the K126A mutation (Table II) nor any of the disulfide variants (not shown) produce significantly more conditions with crystals. The most dramatic difference is upon incorporating the ΔQGTTSΔ (SEQ ID NO: 20) FG loop (i.e., Crystal Kappa design). The Fabs with this design yield crystals in approximately 90-114 conditions out of 192 for the G6 Fab; and approximately 113-136 conditions out of 192 for the dupilumab Fab. Crystals harvested directly out of these screens (i.e. not optimized in subsequent screens) produce high resolution datasets (Table II). The best dupilumab Fab diffract to 1.4 Å from the ΔQGTTSΔ (SEQ ID NO: 20) alone (CK1.0); and the best G6 Fab diffract to 1.15 Å from a combination of the ΔQGTTSΔ (SEQ ID NO: 20) mutation with K126A and the intrachain disulfide (CK1.5).

TABLE II

Crystallization of two Tabs and their variants.

| | HC | LC | G6 Xtal** | G6 Res (Å) | Dup Xtal** | Dup Res (Å) |
|---|---|---|---|---|---|---|
| Parental* | ESKYGH6 (SEQ ID NO: 21) | wild-type Kappa | 1 | | 4 | 2.0 |
| CK0.1 | ESKYGH6 (SEQ ID NO: 21) | K126A | 2 | 3.4 | NA | |

TABLE II-continued

| | | | G6 | | Dup |
|---|---|---|---|---|---|
| | | G6 | Res | Dup | Res |
| HC | LC | Xtal** | (Å) | Xtal** | (Å) |
| CK1.0 | ESKYGH₆ (SEQ ID NO: 21) | ΔQGTTSΔ (SEQ ID NO: 20) | 94 | 1.5 | 113 | 1.4 |
| CK1.1 | ESKYGH₆ (SEQ ID NO: 21) | K126A + ΔQGTTSΔ (SEQ ID NO: 20) | 114 | 1.3 | 136 | 2.1 |
| CK1.2 | ESKYGH₆ (SEQ ID NO: 21) C127A | ΔQGTTSΔ +(SEQ ID NO: 20) + GEP* | 93 | 1.7 | 123 | 1.9 |
| CK1.3 | ESKCGGH₆ (SEQ ID NO: 22) | ΔQGTTSΔ (SEQ ID NO: 20) + GEP* | 90 | 1.2 | 125 | 1.7 |
| CK1.4 | ESKYGH₆ (SEQ ID NO: 21) C127A | K126A + ΔQGTTSΔ +(SEQ ID NO: 21) + GEP* | 104 | 1.4 | NA | |
| CK1.5 | ESKCGGH₆ (SEQ ID NO: 22) | K126A + ΔQGTTSΔ (SEQ ID NO: 20) + GEP* | 110 | 1.15 | 121 | 2.2 |

Crystallization of two Tabs and their variants.

*The parental light chain is the wild-type kappa. The parental heavy chain terminates at the sequence ESKYG and includes H6 tag for purification purposes.
**The "Xtal" column indicates how many conditions from two 96-well screens produce any kind of crystal by approximately day 9. Several crystals are sent from each construct with harvestable crystals and the best resolution dataset is indicated.

Crystal Structures of Engineered Fabs

Fifty-nine datasets are collected for the G6 variants, encompassing 11 crystal forms. Structures are solved for 7 and refined for 5 crystal forms: $P2_12_12_1$ with a 43×75×165 Å cell (5 refined structures), $P4_32_12$ 77×77×330 (3), $P2_12_12_1$ 66×74×91 (1), P1 53×65×67 85×71×84 (1), and C2 206× 103×70 β=92.7° (1). Forty-four datasets are collected for the dupilumab Fab variants, encompassing 11 crystal forms. Structures are solved for four and refined for three datasets: $P2_1$ 53×66×135 β=91.6° (1), $P2_12_12_1$ 59×73×105 (1), $P4_32_12$ 74×74×185 (1).

Figure 1B:
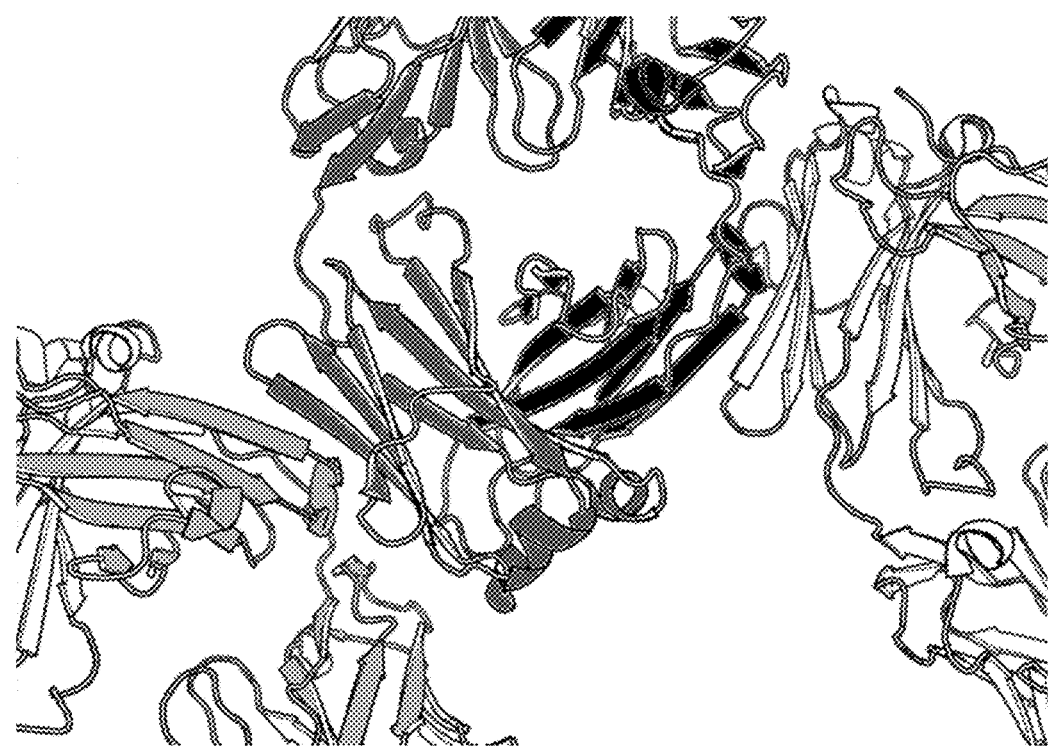
Figure 3A:
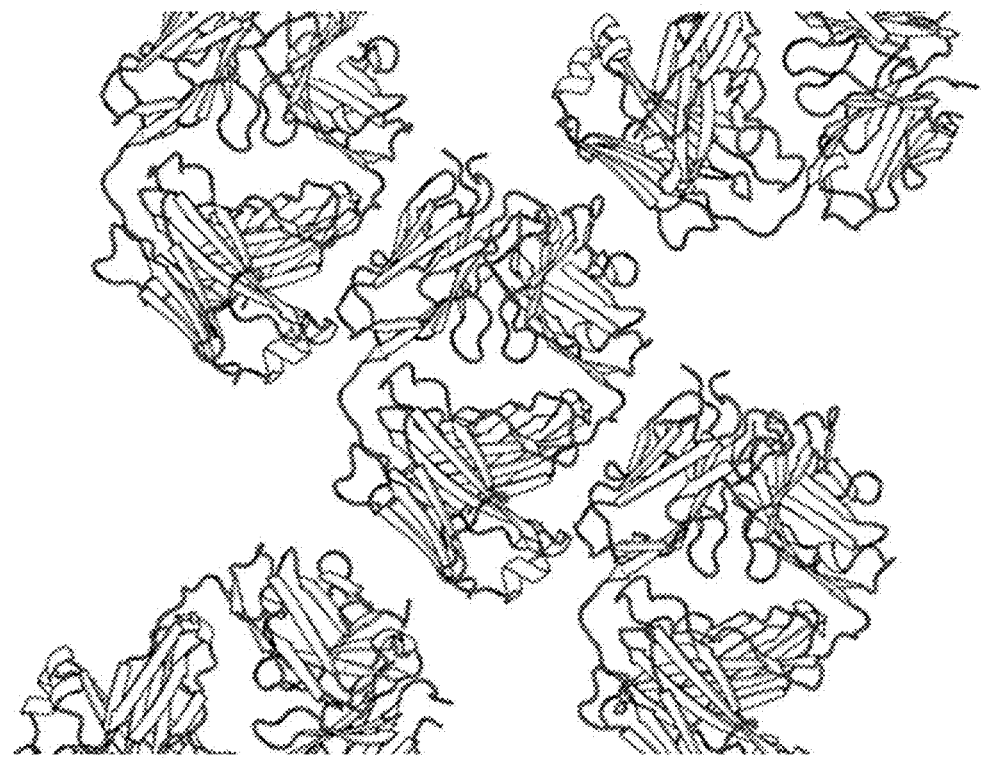
FIGS. 3A-3C show crystal packing in Cκ constructs.
Figure 3B:
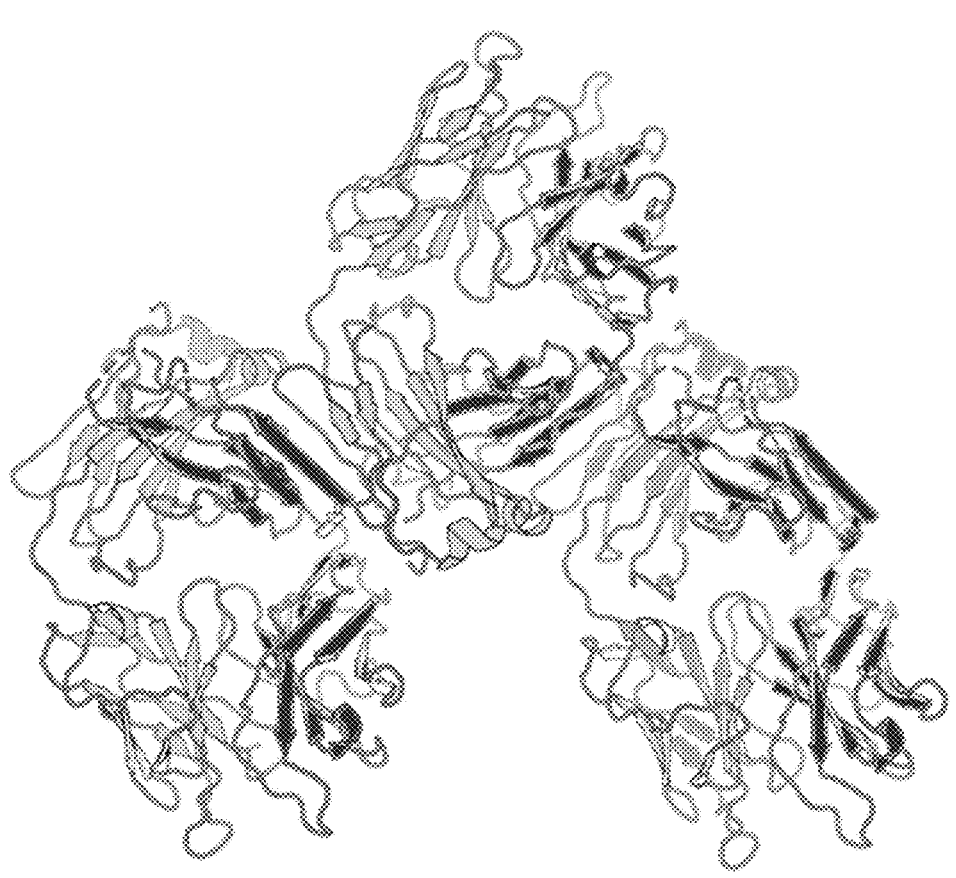
Figure 3C:
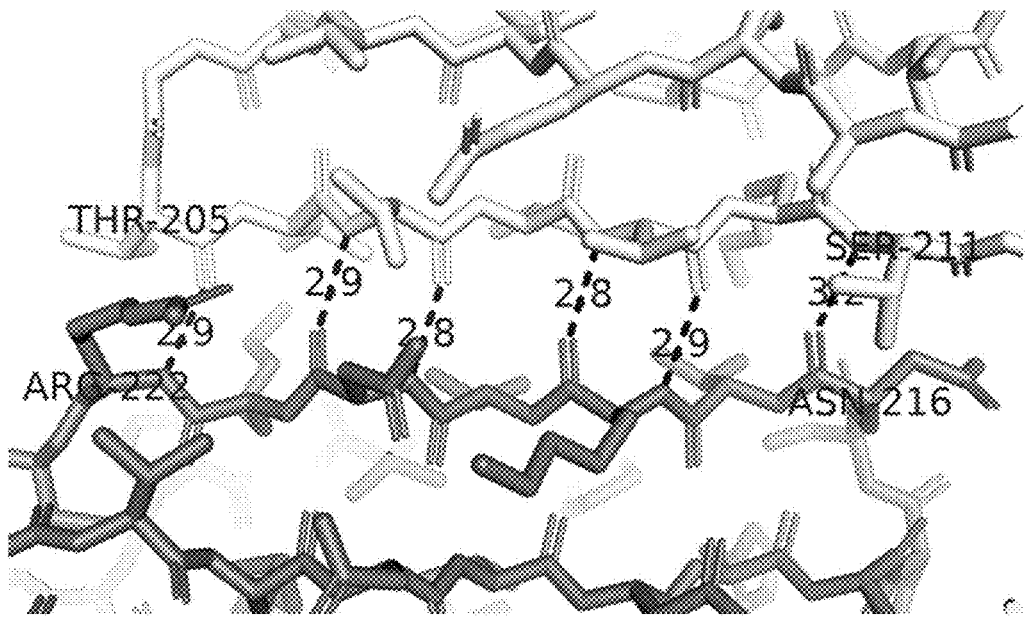

Structures of the Fab variants without the ΔQGTTSΔ (SEQ ID NO: 20), including the parental, do not pack with extended beta sheet interactions. The parental dupilumab Fab for example packs with various types of interactions, but none that form a continuous beta-sheet (FIG. 3A). All structures derived from Fabs with the ΔQGTTSΔ (SEQ ID NO: 20) FG loop on the other hand pack, forming a beta sheet between the G strand of the Cκ domain and the G strand of the CH1 domain (FIGS. 3B and 3C). This interaction is similar but not identical to that is seen in rabbit Fab crystal packing. It involves the same strands as seen in FIG. 1B, but is more extensive, involving 7 residues on both sides like the H: H or L: L interactions seen in FIG. 1A. The pseudo-symmetric center of this beta-sheet is between Cκ V208 (position 205 according to Kabat numbering) and CH1 V219 (Kabat numbering).

The K126A mutation does not appear to impact the crystal packing or diffraction quality. The highest resolution structure for the G6 Fab incorporates this mutation, but the impact of the mutation is not systematic. The highest resolution structure for the dupilumab Fab for example incorporates only the FG loop mutation ΔQGTTSΔ (SEQ ID NO: 20). Nor does the disulfide removal (C127A+GEP*) or intrachain disulfide (ESKC+GEP*) appear to impact crystal packing or diffraction. Structures are obtained with the intrachain disulfide ordered. The temperature factors in this region are higher than average as is seen in other structures with the interchain disulfide ordered.

Crystallization of Fab: Antigen Complexes

Figure 4A:
FIGS. 4A-4B show the crystal structures of the Crystal Kappa designs.
Figure 4B:
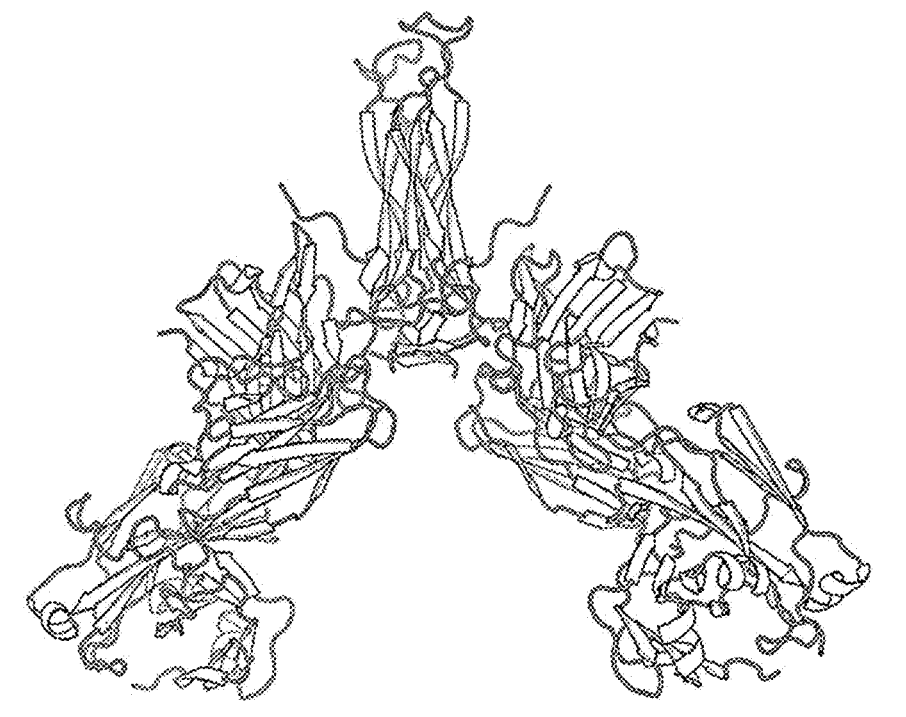

The crystallization mutations are applied to Fab: Antigen complexes. In the case of G6 Fab, the CK1.5 variant of the Fab is utilized since it diffracted the best as a Fab alone. For dupilumab Fab and the other four complexes, the CK1.0 (i.e. only ΔQGTTSΔ (SEQ ID NO: 20)) is utilized. All CH1 domains are IgG4 and have the same C-terminal hexahistidine (H6) tag (SEQ ID NO: 7). None of the parental complexes (i.e. Antigen: Fab complexes without any crystallization engineering applied to the Fab) produce any crystals in the limited screens and time frame employed (Table III). All engineered complexes produce crystals, from 4 conditions (out of 192) for the G6-Receptor complex to 87 conditions for the H4-Receptor complex (FIG. 4C and Table III). Four of the six complexes produce structures, mostly at lower resolution. GITR complex crystals are actually Fab alone upon solving the structure, and the TIGIT complex crystals do not diffract sufficiently well to produce a dataset. The crystals for both dupilumab and secukinumab require optimization to reach their respective 3 and 3.2 Å resolutions (FIGS. 4A-4B). Crystals from the initial screens diffract to 5 Å in the case of the former and not at all for the later.

TABLE III

| | | Parental crystals | CK crystals | Resolution (Å) | Notes | Reference |
|---|---|---|---|---|---|---|
| Fab | Antigen | | | | | |
| G6 | Receptor | 0 | 4 | 3.6 | CK1.5 | Unpublished molecule |
| Dupilumab | IL4Ra | 0 | 34 | 3.0 | optimized | CAS: 1190264-60-8; sequences available at https://www.kegg.jp/entry/D10354 |
| Secukinumab | IL17a | 0 | 54 | 3.2 | optimized | CAS: 1229022-83-6; sequences available at https://www.kegg.jp/entry/D09967 |
| h2155 | GITR | 0 | 54 | 2.6 | Fab only | US2013108641 |
| h22G2 | TIGIT | 0 | 30 | 9 | diffraction only | US2016176963 |
| H4 | Receptor | 0 | 87 | 2.6 | | Unpublished molecule |

Crystallization of Fab:Antigen Complexes.

Complexes are screened in two crystallization screens and scored after 9 days. Number of conditions with crystals of any kind from the parental complex (without crystallization mutations) are indicated in the "parental crystals" column. Conditions with crystals from the CK1.0 Fab antigen complex in the column labelled "CK crystals". The best diffraction or dataset from these screens or subsequent optimizations is indicated in the "Resolution" column.

Because the secukinumab: IL 17 complex produce low resolution but diffracting crystals, it is selected for further comparisons of CH1 domain isotype and C-terminus. Four new constructs are created: an IgG4 version that is 5 residues shorter and ends with the sequence DKRVESK (tagless, SEQ ID NO: 11, residues 95-101), one that ends with DKRVH$_6$ (tagged, SEQ ID NO: 12, residues 95-104), and an IgG1 version ending with the sequence KSC with a H6 tag (SEQ ID NO: 10) or without a H6 tag (SEQ ID NO: 9). These are purified and screened as before at 10 mg/ml but also at 5 mg/ml. The shorter IgG4 versions produce fewer crystals than the original (24 for the tagged and 18 for the untagged versus 54 for the original tagged version). The IgG1 versions give a similar number of conditions with crystals (88 tagged and 43 untagged versus 54 for the original). The 10 mg/ml IgG4 tagged version diffract to 4.2 Å, like the parent that doesn't initially diffract but produces 3.2 Å after optimization. The IgG1 tagged version on the other hand at 10 mg/ml produces a 2.7 Å dataset directly from the initial screen and the IgG1 untagged version at 5 mg/ml produces a 2.4 Å dataset from the initial screen.

Column Fraction Crystallization (CFC)

Figure 5A:
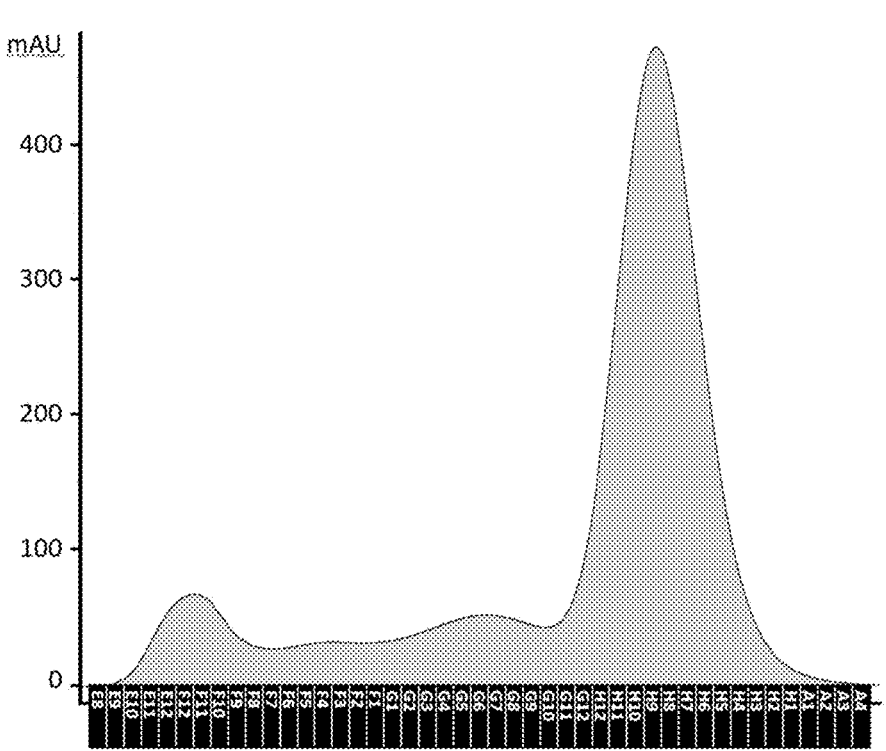
FIGS. 5A-5C show column fraction crystallization. Column fractions from size exclusion chromatography are used directly in a vapor diffusion crystallization experiment in four conditions.
Figure 5B:
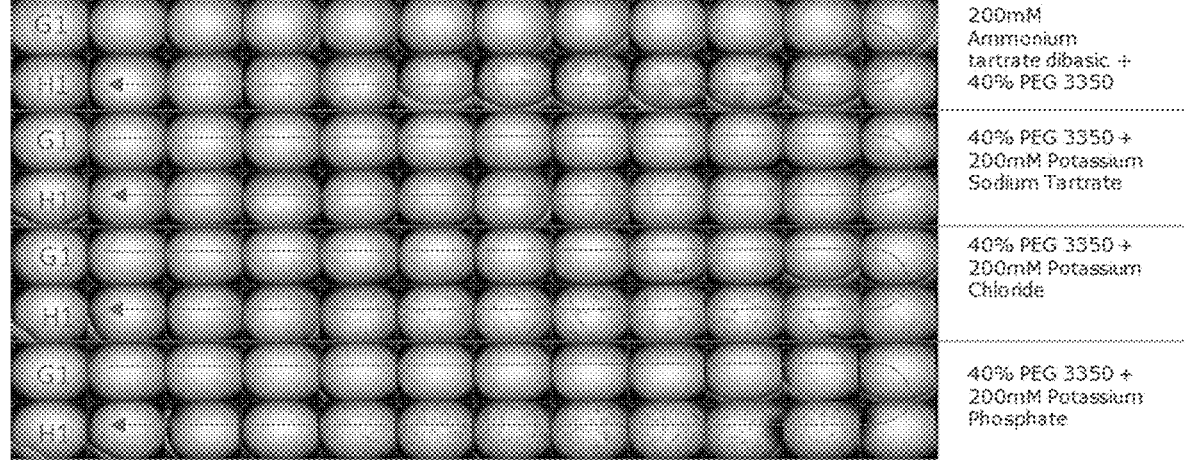
Figure 5C:
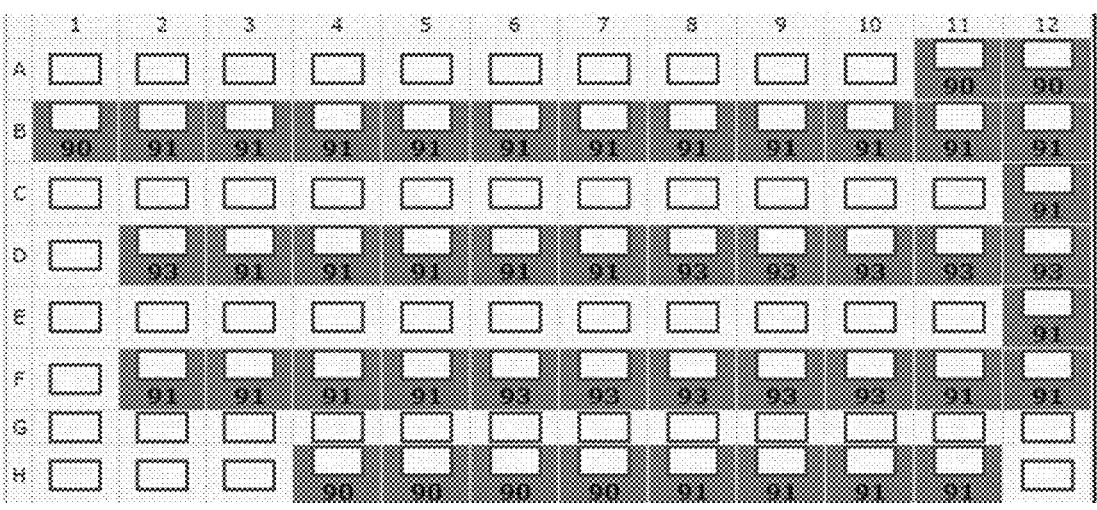

The robust crystallization of the engineered Fabs allows for crystallization directly from column fractions. The ΔQGTTSΔ (SEQ ID NO: 20) variant of G6 Fab produces the same crystal form as the purified and concentrated sample at 10 mg/ml when crystallized directly from column fractions (FIGS. 5A-5C). The CFC structure is at a respectable resolution of 2.4 Å (versus 1.4 Å).

The designs described here were applied to several targets, utilized comparable isotypes and C-termini, used the same purification, crystallization and crystal harvesting procedures (in parallel as much as possible), utilized crystal seeding to reduce variability in nucleation, evaluated crystallization experiments at the same elapsed time, and had the same scientists conduct the purification and crystallization across all experiments.

The variant Cκ domain (ΔQGTTSΔ) (SEQ ID NO: 20) improved the frequency of crystallization by 50-fold for human Fabs. A G6 parental Fab (fully human) yields crystals in only one condition but the G6 variant that contains ΔQGTTSΔ (SEQ ID NO: 20) yields crystals in approximately 90-114 conditions. Dupilumab parental Fab yields crystals in 4 conditions, but Dupilumab variant that contains ΔQGTTSΔ (SEQ ID NO: 20) yields crystals in approximately 113-136 conditions. Furthermore, the modified FG loop of the Cκ domain ("Crystallizable Kappa" or "Crystal Kappa") enabled crystallization of Fab: Antigen complexes, though the fold improvements cannot be calculated because none yield crystals without the Crystal Kappa design. Most Crystal Kappa versions yield between 30 and 90 crystalizing conditions for the complex (note: statistics are from two plates at one relatively conservative time point).

Relative to the Fab results, results with the complexes are less encouraging. While the complexes using Crystal Kappa all produce crystals, a significant advantage to any effort, only 4 out of 6 yield complex datasets good enough to solve and refine, and these tend towards lower resolutions. One (h2155+GITR) produces crystals of the Fab alone.

The 3.0 Å structure of Dupilumab Fab complexed with human IL4R shows an epitope that substantially overlaps with IL4 and IL13 binding, explaining its blocking activity (FIG. 4A). The central part of the epitope is the CD loop (Ul-Haq 2016), explaining why Dupilumab has no cross-reactivity with Cynomolgus monkey IL4R which has a very different sequence in this region ($L_{67}L_{68}$ VS. $Q_{67}S_{68}$). The 3.0 Å Secukinumab IL17 complex (and its 2.4 Å improved structure) shows two Fabs bound to the IL 17 dimer with a discontinuous epitope, each Fab binding portions of both IL17 chains (FIG. 4B). The H4 complex produces a crystal packing arrangement with 3 Fabs in the asymmetric unit (not shown). One of the Fabs forms two HC:LC beta packing interactions typical for the Cκ design. Another Fab forms one on the LC side and nothing on the HC side. And the third Fab forms a HC:LC interaction with the second and its LC forms a LC:LC beta packing interaction, the only such interaction has been seen.

An additional refinement of the secukinumab constructs shortens the C-terminus of the IgG4 construct and includes IgG1 versions for the first time and compared Ho tagged versus untagged versions. 10 mg/ml is compared to 5 mg/ml to make the crystals less crowded for harvesting purposes. In this series, the IgG1 versions behave better than the IgG4 and yield a 2.7 Å dataset for the tagged (at 10 mg/ml) and 2.4 Å dataset for the untagged Fab (at 5 mg/ml) versions directly, whereas the 3.0 Å dataset from the CK1.0 construct is obtained after optimization and screening of numerous crystals. Interestingly the G1, G4 (two versions), tagged and tagless, all produce isomorphous crystals.

With regard to speed of crystallization, all the crystals described grow within a week, and for those checked more frequently, crystals appear within hours. With regard to concentration, the column fraction crystallization experiment shows that it is possible to obtain crystals from samples as dilute as 0.1 mg/ml, at least for Fabs alone. Besides the implications for required concentrations, the CFC has other potential advantages. For example, the character of the protein at the leading edge of a column peak is probably different from the trailing edge and one or the other might be more productive in determining a structure. The CFC experiment and the fact that Fabs crystallize in more than half of crystallization conditions at high concentrations suggest that for Fabs the Crystal Kappa design should allow for a dramatically simplified set of screening conditions.

In conclusion, crystallizable variants of the human constant kappa domain (variant Cκ) are provided herein, which dramatically improve the frequency of crystal formation for Fabs and Fab: Antigen complexes, yield high resolution structures for Fabs (and Fab: peptide complexes) and can yield in most cases at least low resolution datasets and structures of Fab: protein complexes. The Crystal Kappa designs appear to allow for overnight crystallization from dilute samples in screens of a handful of conditions. Crystal Kappa designs should make Fab structure determination robust even using smaller screens and less protein and speed up complex structure determination, including Fab chaperone complexes with difficult targets.

Materials and Methods

Engineering and Molecular Biology

Analysis of rabbit Fab crystal packing is conducted in Pymol utilizing structures available in the Protein Databank and Eli Lilly's proprietary structural database. Alignment of LC constant domains from various species utilizes BLAST. Amino acid sequence for the variable domains of Dupilumab and Secukinumab are obtained from the Kyoto Encyclopedia of Genes and Genomes website (www.kegg.jp; Kanehisa 2000), entries D10354 and D09967. Sequences for h2155 and h22G2 are obtained from patents US2013108641 and US2016176963. Expression vectors are created by synthesizing the corresponding DNA fragments as gblocks (IDT, Coralville IA) and cloning into mammalian expression vectors using standard techniques.

Expression and Purification

Fabs and antigen ECDs are expressed in mammalian cell culture CHO cells. Protein containing cell culture supernatants are harvested and clarified media is purified by Immobilized Metal Affinity Chromatography (IMAC) using His Trap™ Excel (GE Healthcare) using PBS buffer plus 15 mM Imidazole, pH 7.5 as the binding buffer. The proteins are then eluted on a 10 column volume gradient elution in PBS plus 0.3M Imidazole, pH 7.4. The eluents are collected and concentrated using a Millipore 10 KDa spin concentrator. The concentrate IMAC pools are loaded on either a Superdex75 or Superdex200 (GE Healthcare) columns. Proteins are concentrated again to 10 mg/ml for crystallization trays.

The proteins are characterized by analytical size exclusion chromatography (Waters) and SDS-PAGE gel (data not shown).

Crystallization and Structure Determination

All samples are concentrated to 5-10 mg/ml and are set up at room temperature in vapor diffusion sitting drops at a ratio of 1:1 using Qiagen Classics II and PEGs crystallization screens. Drops are immediately cross seeded with related Fab crystal seeds for the Fabs crystallization and complex-crystal seeds for complex crystallization. Images of crystallization trays are taken on day 1, day 4, and day 9. Prior to freezing in liquid nitrogen, crystals are transferred to a cryoprotectant solution consisting either of well solution supplemented with an additional 10% of the precipitant used in that crystallization well and 25% of glycerol or from the mother liquor, if it includes a precipitant with cryoprotecting qualities (such as PEG 400, PEG MME 550, PEG MME 2K etc.) in concentrations sufficient for cryoprotection.

Structure determination diffraction datasets are collected at the following sources: Lilly Research Collaborative Access Team (LRL-CAT) Beamline 31-ID at Advanced Proton Source (Argonne, IL); Beamline ALS-502 at Advanced Light Source (Berkley, CA); Beamline I04-1 at Diamond Light Source (Oxfordshire, UK). Data are integrated and reduced using MOSFLM (Leslie A G W & Powell H R. In: Read R J, & Sussman J L (Eds.), Evolving methods for macromolecular crystallography: the structural path to the understanding of the mechanism of action of CBRN Agents. Dordrecht: Springer Netherlands. 2007) and the CCP4 suite of programs (Winn, et al., Acta Crystallogr D Biol Crystallogr, 2011. 67 (Pt 4): 235-42). Initial molecular replacement solutions are obtained using Phaser (CCP4 suite) (McCoy, et al., J. Appl. Crystallogr., 2007. 40 (Pt 4): 658-674). The model is built using COOT (Emsley, et al., Acta Crystallogr D Biol Crystallogr, 2010. 66 (Pt 4): 486-501) and refined using Refmac (Murshudov, et al., Acta Crystallogr D Biol Crystallogr, 2011. 67 (Pt 4): 355-67) or Buster (Bricogne, et al. BUSTER version 2.11.5. Cambridge, United Kingdom: Global Phasing Ltd. 2011) and validated using internal developed protocols.

Example 2: Crystallization and X-Ray Structure Determination of Full-Length Monoclonal Antibody (mAb)

In addition to Fab fragments, the Crystal Kappa design can be utilized to crystallize full-length IgG antibodies as follows. The light chain of the antibody is modified with the Crystal Kappa design in standard expression vectors using standard molecular biology techniques. The light chain is then expressed with the corresponding heavy chain in an expression system appropriate for secreting antibodies, e.g. HEK293 or Chinese Hamster Ovary cells. The antibody is then purified from the media using techniques such as column purification with a MabSelect column (GE Healthcare) and concentrated to, e.g., 5 mgs/ml. Utilizing the method of vapor diffusion, conditions are then screened for the growth of protein crystals from the purified antibody. Crystals are then isolated, transferred and frozen before X-ray data is collected. Using standard techniques, the structure can then be determined from that data by molecular replacement, e.g. using the software Phaser and then the atomic model refined.

One antibody structure resulted from incorporating the Crystal Kappa design into the kappa light chain of an IgG4-P (IgG4 with S241P according to Kabat numbering, or S228P according to EU index numbering) isotype antibody. From a 96-well screen (ComPAS, Qiagen) at 21° C., several conditions yielded crystals including 18% ethanol+100 mM Tris HCl (pH 8.5). By optimizing these conditions diffracting crystals and a 4 Å dataset was obtained from 20% ethanol, 21° C. The molecular replacement solution of this dataset yielded the structure of a full-length antibody (two heavy chains, two light chains and glycosylation), whose conformation differed significantly from the conformations of the two known human IgG4 structures (5DK3.pdb & 6GFE.pdb) and is more similar to the known human IgG1 structure (1HZH.pdb). The Crystal Kappa design contributed to crystal packing as did other contact points in the antibody.

Figure 6A:
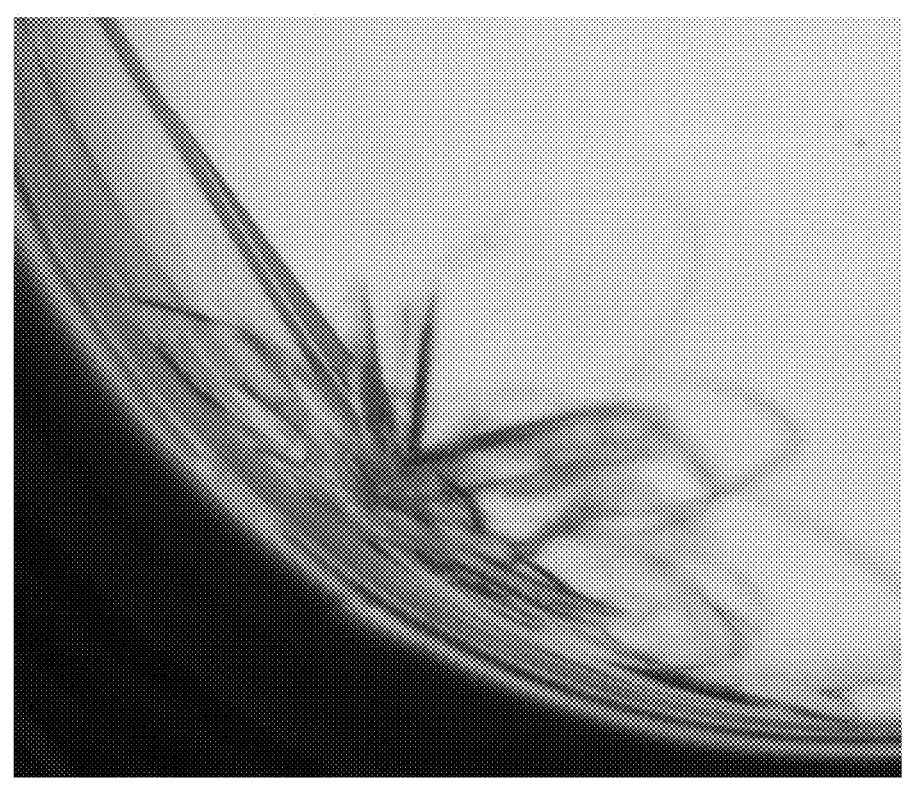
FIGS. 6A-6B show crystallization and structure determination of a full-length mAb using the Crystal Kappa design.
Figure 6B:

FIGS. 6A-6B show the crystallization and structure determination of the full-length mAb. FIG. 6A is an image showing the crystals of the full-length mAb. FIG. 6B is a ribbon diagram of the resulting structure with the antibody heavy chain in black (including Fc glycosylation in sticks) and antibody light chain in light gray.

Example 3: Crystallization of Fab: Antigen Peptide Complexes by Generation of Fusion Protein The crystal structure determination of Fabs in complex with its antigen peptide can be achieved in two ways. First and more typically, the antigen peptide can be purchased or prepared using a variety of techniques (Chandrudu S, Simerska P, Toth I. Chemical methods for peptide and protein production. Molecules. 2013 Apr. 12; 18 (4): 4373-88). This peptide can then be solubilized and added to the Fab at a final concentration that equals or exceeds the Fab concentration in molar terms. Crystallization and structure determination of the complex is then achieved as for a Crystal Kappa Fab alone. The second technique, which obviates the need to purchase the peptide, is to insert the encoding sequence for the peptide directly into the open reading frame of either the Fd or the kappa light chain to generate a fusion protein with an appropriate linker between the peptide and the Fd/kappa light chain during construction of the Fab expression vector(s). In the fusion protein, the peptide will then be tethered to the Fab by the linker with an exact one-to-one stoichiometry. The tethering also has the benefit of increasing the effective concentration of the peptide and avoiding the situation where a low affinity peptide does not appear in the crystal or resulting structure. Tethering guarantees the presence of the antigen peptide in the crystal.

The Fab: Antigen peptide complex was obtained for the anti-Tau antibody L14H18 (WO 2017/005734) with its cognate Tau peptide antigen as follows. A tau peptide (amino acids 231-250) encompassing the known epitope, TPPK-SPSSAKSRLQTAPVPM (SEQ ID NO: 18), was fused to the N-terminus of either the Fd-His6 or the Crystal Kappa light chain of the L14H18 Fab with a GS linker (SEQ ID NO: 19) by incorporating a DNA sequence that translates into those 27 amino acids in between the signal sequence of the open reading frame and the mature beginning of the Fab chains. Both the Tau peptide-linker-Fd-His/Crystal Kappa light chain and the Fd-His/Tau peptide-linker-Crystal Kappa light chain versions were expressed in CHO cells, purified by immobilized metal affinity chromatography and gel filtration, concentrated to 4.5 mgs/ml and crystallized in commercially available screens. Dozens of conditions produced crystals for both versions in the Classics and PEGs screens (Qiagen). Two complex structures were solved and refined for the Crystal Kappa fusion: a 1.22 Å structure from 20% PEG 3350/200 mM Potassium Sodium Tartrate and a 2.3 Å structure from 100 mM Sodium Acetate pH 4.6/25% PEG 4000/200 mM Ammonium Sulfate. Both of the structures showed a mostly extended peptide with one helical turn bound to the CDRs of the Fab and differed only in the extent of order in the linker portion.

Figure 7A:
FIGS. 7A-7B show crystallization of a peptide-Fab complex using the Crystal Kappa design.
Figure 7B:
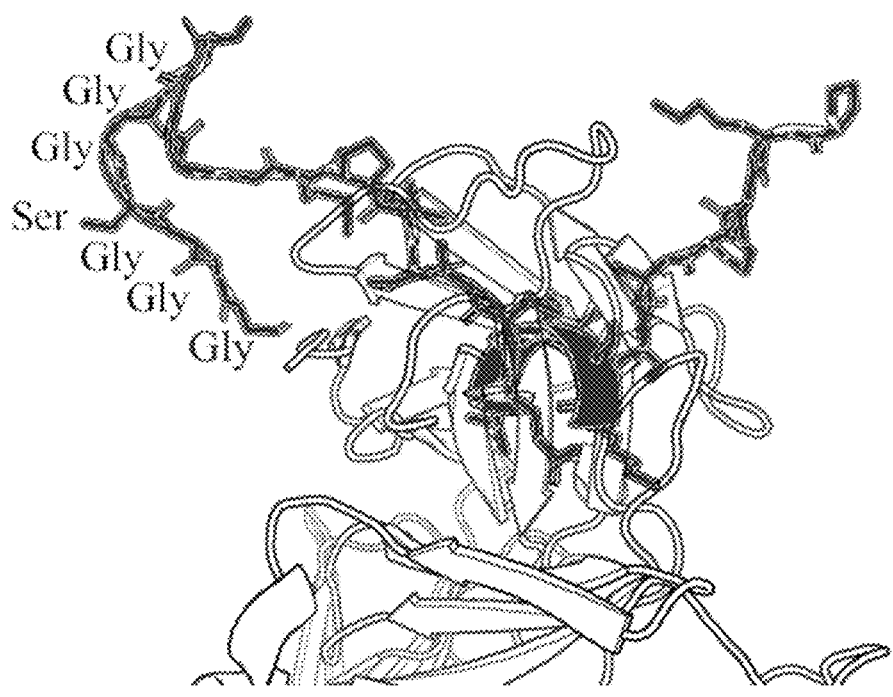

FIGS. 7A-7B show crystallization of the Tau peptide-Fab complex. FIG. 7A is an image showing the crystals of the Crystal Kappa light chain of L14H18 fused to the Tau peptide after four hours. FIG. 7B is a ribbon diagram of the resulting 2.3 Å structure of the Tau peptide (white) bound to L14H18 Fab with a mostly ordered GS linker to the N-terminus of the Fab light chain (gray). Fab heavy chain is shown in black.

```
SEQUENCE LISTING
Wild type human kappa light chain constant domain
(CK) amino acid sequence
                                (SEQ ID NO: 1)
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC Human CK K126A variant amino acid sequence
                                (SEQ ID NO: 2)
RTVAAPSVFIFPPSDEQLASGTASVVCLLNNFYPREAKVQWKVDNALQS
GNSQESVTEQDSKDSTYSLSSTLTLSKADYEKHKVYACEVTHQGLSSPV
TKSFNRGEC Human CK ΔQGTTSΔ (SEQ ID NO: 20) variant amino
acid sequence
                                (SEQ ID NO: 3)
RTVAAPSVFIFPPSDEQLKSGTASVVCLLNNFYPREAKVQWKVDNALQS
GNSQESVTEQDSKDSTYSLSSTLTLSKADYEKHKVYACEVTQGTTSVTK
SFNRGEC Human CK K126A + ΔQGTTSΔ (SEQ ID NO: 20) variant
amino acid sequence
                                (SEQ ID NO: 4)
RTVAAPSVFIFPPSDEQLASGTASVVCLLNNFYPREAKVQWKVDNALQS
GNSQESVTEQDSKDSTYSLSSTLTLSKADYEKHKVYACEVTQGTTSVTK
SFNRGEC Human CK ΔQGTTSΔ (SEQ ID NO: 20) + GEP* variant
amino acid sequence
                                (SEQ ID NO: 5)
RTVAAPSVFIFPPSDEQLKSGTASVVCLLNNFYPREAKVQWKVDNALQS
GNSQESVTEQDSKDSTYSLSSTLTLSKADYEKHKVYACEVTQGTTSVTK
SFNRGEP Human CK K126A + ΔQGTTSΔ (SEQ ID NO: 20) + GEP*
variant amino acid sequence
                                (SEQ ID NO: 6)
RTVAAPSVFIFPPSDEQLASGTASVVCLLNNFYPREAKVQWKVDNALQS
GNSQESVTEQDSKDSTYSLSSTLTLSKADYEKHKVYACEVTQGTTSVTK
SFNRGEP Human IgG4 CH1 domain ESKYGH6 (SEQ ID NO: 21)
variant amino acid sequence
                                (SEQ ID NO: 7)
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGHHHHHH Human IgG4 CH1 domain ESKYGH6 (SEQ ID NO: 21) +
C127A variant amino acid sequence
                                (SEQ ID NO: 8)
ASTKGPSVFPLAPASRSTSESTAALGCLVKDYFPEPVTVSWNSGALTSG
VHTFPAVLQSSGLYSLSSVVTVPSSSLGTKTYTCNVDHKPSNTKVDKRV
ESKYGHHHHHH Wild type human IgG1 tagless CH1 domain amino acid
sequence
                                (SEQ ID NO: 9)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSC Human IgG1 tagged CH1 domain amino acid sequence
                                (SEQ ID NO: 10)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCHHHHHH Human IgG4 tagless CH1 domain
                                (SEQ ID NO: 11)
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESK
```

Human IgG4 tagged CH1 domain
```
                                    (SEQ ID NO: 12)
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
HHHHHH
```

Wild type mouse Cκ amino acid sequence
```
                                    (SEQ ID NO: 13)
RADAAPTVSIFPPSSEQLTSGGASVVCFLNNFYPKDINVKWKIDGSERQ
NGVLNSWTDQDSKDSTYSMSSTLTLTKDEYERHNSYTCEATHKTSTSPI
VKSFNRNEC
```

Wild type rabbit Cκ amino acid sequence
```
                                    (SEQ ID NO: 14)
GDPVAPTVLIFPPAADQVATGTVTIVCVANKYFPDVTVTWEVDGTTQTT
GIENSKTPQNSADCTYNLSSTLTLTSTQYNSHKEYTCKVTQGTTSVVQS
FNRGDC
```

Wild type human lambda light chain constant domain
(CA) amino acid sequence
```
                                    (SEQ ID NO: 15)
GQPKANPTVTLFPPSSEELQANKATLVCLISDFYPGAVTVAWKADGSPV
KAGVETTKPSKQSNNKYAASSYLSLTPEQWKSHRSYSCQVTHEGSTVEK
TVAPTECS
```

Wild type mouse CA amino acid sequence
```
                                    (SEQ ID NO: 16)
QPKSSPSVTLFPPSSEELETNKATLVCTITDFYPGVVTVDWKVDGTPVT
QGMETTQPSKQSNNKYMASSYLTLTARAWERHSSYSCQVTHEGHTVEKS
LSRADCS
```

Wild type rabbit CA amino acid sequence
```
                                    (SEQ ID NO: 17)
QPAVTPSVILFPPSSEELKDNKATLVCLISDFYPRTVKVNWKADGNSVT
QGVDTTQPSKQSNNKYAASSFLHLTANQWKSYQSVTCQVTHEGHTVEKS
LAPAECS
```

Tau peptide
```
                                    (SEQ ID NO: 18)
TPPKSPSSAKSRLQTAPVPM
```

GS linker
```
                                    (SEQ ID NO: 19)
GGGSGGG
```

Crystal Kappa Design
```
                                    (SEQ ID NO: 20)
QGTTS
```

ESKYGH$_6$ Design
```
                                    (SEQ ID NO: 21)
ESKYGHHHHHH
```

ESKCGGH$_6$ Design
```
                                    (SEQ ID NO: 22)
ESKCGGHHHHHH
```

Septamer Sequence
```
                                    (SEQ ID NO: 23)
HQGLSSP
```

---

The invention claimed is:

1. A human Fab or Fab' comprising a variant Cκ, wherein the variant Cκ comprises the sequence selected from SEQ ID NO: 3, SEQ ID NO: 4, SEQ ID NO: 5, or SEQ ID NO: 6.

2. The human Fab or Fab' of claim 1, wherein the variant Cκ comprises the sequence of SEQ ID NO: 3.

3. The human Fab or Fab' of claim 1, wherein the variant Cκ comprises the sequence of SEQ ID NO: 4.

4. The human Fab or Fab' of claim 1, wherein the variant Cκ comprises the sequence of SEQ ID NO: 5.

5. The human Fab or Fab' of claim 1, wherein the variant Cκ comprises the sequence of SEQ ID NO: 6.

6. The human Fab or Fab' of claim 1, wherein the human Fab or Fab' further comprises a human light chain variable domain (VL) and a human heavy chain variable domain (VH).

7. The human Fab or Fab' of claim 1, wherein the human Fab or Fab' further comprises a human IgG CH1 domain.

8. The human Fab or Fab' of claim 7, wherein the human IgG CH1 domain is a human IgG1 or IgG4 CH1 domain.

9. A monoclonal antibody or fusion protein comprising the human Fab or Fab' of claim 1.

10. The human Fab or Fab' of claim 1, wherein the variant Cκ consists of the sequence of SEQ ID NO: 3.

11. The human Fab or Fab' of claim 1, wherein the variant Cκ consists of the sequence of SEQ ID NO: 4.

12. The human Fab or Fab' of claim 1, wherein the variant Cκ consists of the sequence of SEQ ID NO: 5.

13. The human Fab or Fab' of claim 1, wherein the variant Cκ consists of the sequence of SEQ ID NO: 6.

* * * * *

SEQUENCE LISTING

```
<160> NUMBER OF SEQ ID NOS: 23

<210> SEQ ID NO 1
<211> LENGTH: 107
<212> TYPE: PRT
<213> ORGANISM: homo sapiens

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Synthetic Construct

<400> SEQUENCE: 2

Arg Thr Val Ala Ala Pro Ser Val Phe Ile Phe Pro Pro Ser Asp Glu
1               5                   10                  15
```

-continued

```
Gln Leu Ala Ser Gly Thr Ala Ser Val Val Cys Leu Leu Asn Asn Phe
        20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 3
<211> LENGTH: 105
<212> TYPE: PRT
<213> ORGANISM: ARTIFICIAL SEQUENCE
<220> FEATURE:
<223> OTHER INFORMATION: Synthetic Construct

<400> SEQUENCE: 3

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
        20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr Gln Gly Thr Thr Ser Val
                85                  90                  95

Thr Lys Ser Phe Asn Arg Gly Glu Cys
            100                 105

<210> SEQ ID NO 4
<211> LENGTH: 105
<212> TYPE: PRT
<213> ORGANISM: ARTIFICIAL SEQUENCE
<220> FEATURE:
<223> OTHER INFORMATION: Synthetic Construct

<400> SEQUENCE: 4

Arg Thr Val Ala Ala Pro Ser Val Phe Ile Phe Pro Pro Ser Asp Glu
1               5                   10                  15

Gln Leu Ala Ser Gly Thr Ala Ser Val Val Cys Leu Leu Asn Asn Phe
        20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr Gln Gly Thr Thr Ser Val
                85                  90                  95

Thr Lys Ser Phe Asn Arg Gly Glu Cys
            100                 105
```

-continued

```
<210> SEQ ID NO 5
<211> LENGTH: 105
<212> TYPE: PRT
<213> ORGANISM: ARTIFICIAL SEQUENCE
<220> FEATURE:
<223> OTHER INFORMATION: Synthetic Construct

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr Gln Gly Thr Thr Ser Val
                85                  90                  95

Thr Lys Ser Phe Asn Arg Gly Glu Pro
            100                 105

<210> SEQ ID NO 6
<211> LENGTH: 105
<212> TYPE: PRT
<213> ORGANISM: ARTIFICIAL SEQUENCE
<220> FEATURE:
<223> OTHER INFORMATION: Synthetic Construct

<400> SEQUENCE: 6

Arg Thr Val Ala Ala Pro Ser Val Phe Ile Phe Pro Pro Ser Asp Glu
1               5                   10                  15

Gln Leu Ala Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr Gln Gly Thr Thr Ser Val
                85                  90                  95

Thr Lys Ser Phe Asn Arg Gly Glu Pro
            100                 105

<210> SEQ ID NO 7
<211> LENGTH: 109
<212> TYPE: PRT
<213> ORGANISM: ARTIFICIAL SEQUENCE
<220> FEATURE:
<223> OTHER INFORMATION: Synthetic Construct

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
                85              90              95

Arg Val Glu Ser Lys Tyr Gly His His His His His His
            100             105
```

<210> SEQ ID NO 8
<211> LENGTH: 109
<212> TYPE: PRT
<213> ORGANISM: ARTIFICIAL SEQUENCE
<220> FEATURE:
<223> OTHER INFORMATION: Synthetic Construct

<400> SEQUENCE: 8

```
Ala Ser Thr Lys Gly Pro Ser Val Phe Pro Leu Ala Pro Ala Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
                85              90              95

Arg Val Glu Ser Lys Tyr Gly His His His His His
            100             105
```

<210> SEQ ID NO 9
<211> LENGTH: 103
<212> TYPE: PRT
<213> ORGANISM: homo sapiens

<400> SEQUENCE: 9

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys
            100
```

<210> SEQ ID NO 10
<211> LENGTH: 109
<212> TYPE: PRT

<213> ORGANISM: ARTIFICIAL SEQUENCE
<220> FEATURE:
<223> OTHER INFORMATION: Synthetic Construct

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys His His His His His His
            100                 105
```

<210> SEQ ID NO 11
<211> LENGTH: 101
<212> TYPE: PRT
<213> ORGANISM: homo sapiens

<400> SEQUENCE: 11

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys
            100
```

<210> SEQ ID NO 12
<211> LENGTH: 104
<212> TYPE: PRT
<213> ORGANISM: ARTIFICIAL SEQUENCE
<220> FEATURE:
<223> OTHER INFORMATION: Synthetic Construct

<400> SEQUENCE: 12

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
```

-continued

```
65                  70                  75                  80

Tyr Thr Cys Asn Val Asp His Lys Pro Ser Asn Thr Lys Val Asp Lys
                85                  90                  95

Arg Val His His His His His His
            100

<210> SEQ ID NO 13
<211> LENGTH: 107
<212> TYPE: PRT
<213> ORGANISM: Mus musculus

<400> SEQUENCE: 13

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
                20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 14
<211> LENGTH: 104
<212> TYPE: PRT
<213> ORGANISM: Oryctolagus cuniculus

<400> SEQUENCE: 14

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
                20                  25                  30

Phe Pro Asp Val Thr Val Thr Trp Glu Val Asp Gly Thr Thr Gln Thr
            35                  40                  45

Thr Gly Ile Glu Asn Ser Lys Thr Pro Gln Asn Ser Ala Asp Cys Thr
        50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 15
<211> LENGTH: 106
<212> TYPE: PRT
<213> ORGANISM: homo sapiens

<400> SEQUENCE: 15

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30
```

-continued

```
Phe Tyr Pro Gly Ala Val Thr Val Ala Trp Lys Ala Asp Gly Ser Pro
        35              40              45

Val Lys Ala Gly Val Glu Thr Thr Lys Pro Ser Lys Gln Ser Asn Asn
    50              55              60

Lys Tyr Ala Ala Ser Ser Tyr Leu Ser Leu Thr Pro Glu Gln Trp Lys
65              70              75              80

Ser His Arg Ser Tyr Ser Cys Gln Val Thr His Glu Gly Ser Thr Val
                85              90              95

Glu Lys Thr Val Ala Pro Thr Glu Cys Ser
            100             105

<210> SEQ ID NO 16
<211> LENGTH: 105
<212> TYPE: PRT
<213> ORGANISM: Mus musculus

<400> SEQUENCE: 16

Gln Pro Lys Ser Ser Pro Ser Val Thr Leu Phe Pro Pro Ser Ser Glu
1               5               10              15

Glu Leu Glu Thr Asn Lys Ala Thr Leu Val Cys Thr Ile Thr Asp Phe
            20              25              30

Tyr Pro Gly Val Val Thr Val Asp Trp Lys Val Asp Gly Thr Pro Val
        35              40              45

Thr Gln Gly Met Glu Thr Thr Gln Pro Ser Lys Gln Ser Asn Asn Lys
    50              55              60

Tyr Met Ala Ser Ser Tyr Leu Thr Leu Thr Ala Arg Ala Trp Glu Arg
65              70              75              80

His Ser Ser Tyr Ser Cys Gln Val Thr His Glu Gly His Thr Val Glu
                85              90              95

Lys Ser Leu Ser Arg Ala Asp Cys Ser
            100             105

<210> SEQ ID NO 17
<211> LENGTH: 105
<212> TYPE: PRT
<213> ORGANISM: Artificial Sequence
<220> FEATURE:
<223> OTHER INFORMATION: Synthetic Construct

<400> SEQUENCE: 17

Gln Pro Ala Val Thr Pro Ser Val Ile Leu Phe Pro Pro Ser Ser Glu
1               5               10              15

Glu Leu Lys Asp Asn Lys Ala Thr Leu Val Cys Leu Ile Ser Asp Phe
            20              25              30

Tyr Pro Arg Thr Val Lys Val Asn Trp Lys Ala Asp Gly Asn Ser Val
        35              40              45

Thr Gln Gly Val Asp Thr Thr Gln Pro Ser Lys Gln Ser Asn Asn Lys
    50              55              60

Tyr Ala Ala Ser Ser Phe Leu His Leu Thr Ala Asn Gln Trp Lys Ser
65              70              75              80

Tyr Gln Ser Val Thr Cys Gln Val Thr His Glu Gly His Thr Val Glu
                85              90              95

Lys Ser Leu Ala Pro Ala Glu Cys Ser
            100             105

<210> SEQ ID NO 18
<211> LENGTH: 20
```

-continued

```
<212> TYPE: PRT
<213> ORGANISM: Artificial Sequence
<220> FEATURE:
<223> OTHER INFORMATION: Synthetic Construct

<400> SEQUENCE: 18

Thr Pro Pro Lys Ser Pro Ser Ser Ala Lys Ser Arg Leu Gln Thr Ala
1               5                   10                  15

Pro Val Pro Met
            20

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Gly Gly Gly Ser Gly Gly Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Gln Gly Thr Thr Ser
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21

Glu Ser Lys Tyr Gly His His His His His His
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Glu Ser Lys Cys Gly Gly His His His His His His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

His Gln Gly Leu Ser Ser Pro
1               5
```